United States Patent [19]

Mogelof

[11] Patent Number: 4,715,816

[45] Date of Patent: Dec. 29, 1987

[54] ADJUSTABLE DENTAL WEDGING SYSTEM

[76] Inventor: Andrew Mogelof, 298B South Trail, Stratford, Conn. 06497

[21] Appl. No.: 900,302

[22] Filed: Aug. 25, 1986

[51] Int. Cl.$^4$ ............................................... A61C 7/00
[52] U.S. Cl. ....................................................... 433/149
[58] Field of Search ........................... 433/40, 148, 149

[56] References Cited

U.S. PATENT DOCUMENTS

| 819,136 | 5/1906 | Herman | 433/149 |
| 2,867,905 | 1/1959 | Meacham | 433/169 |
| 4,259,070 | 3/1981 | Soelberg et al. | 433/169 |
| 4,578,035 | 3/1986 | Pruitt | 433/169 |

Primary Examiner—Robert Peshock
Attorney, Agent, or Firm—Kramer, Brufsky & Cifelli

[57] ABSTRACT

A dental wedging system includes an adjustable wedge characterized by a central bore positioned along a longitudinal axis of the wedge. A pair of opposed leaves separate along an apex of the wedge. A piston is used to variably separate the leaves. The adjustable dental wedging system can be used in conjunction with composite dental fibers for ensuring adequate inter-tooth separation.

7 Claims, 2 Drawing Figures

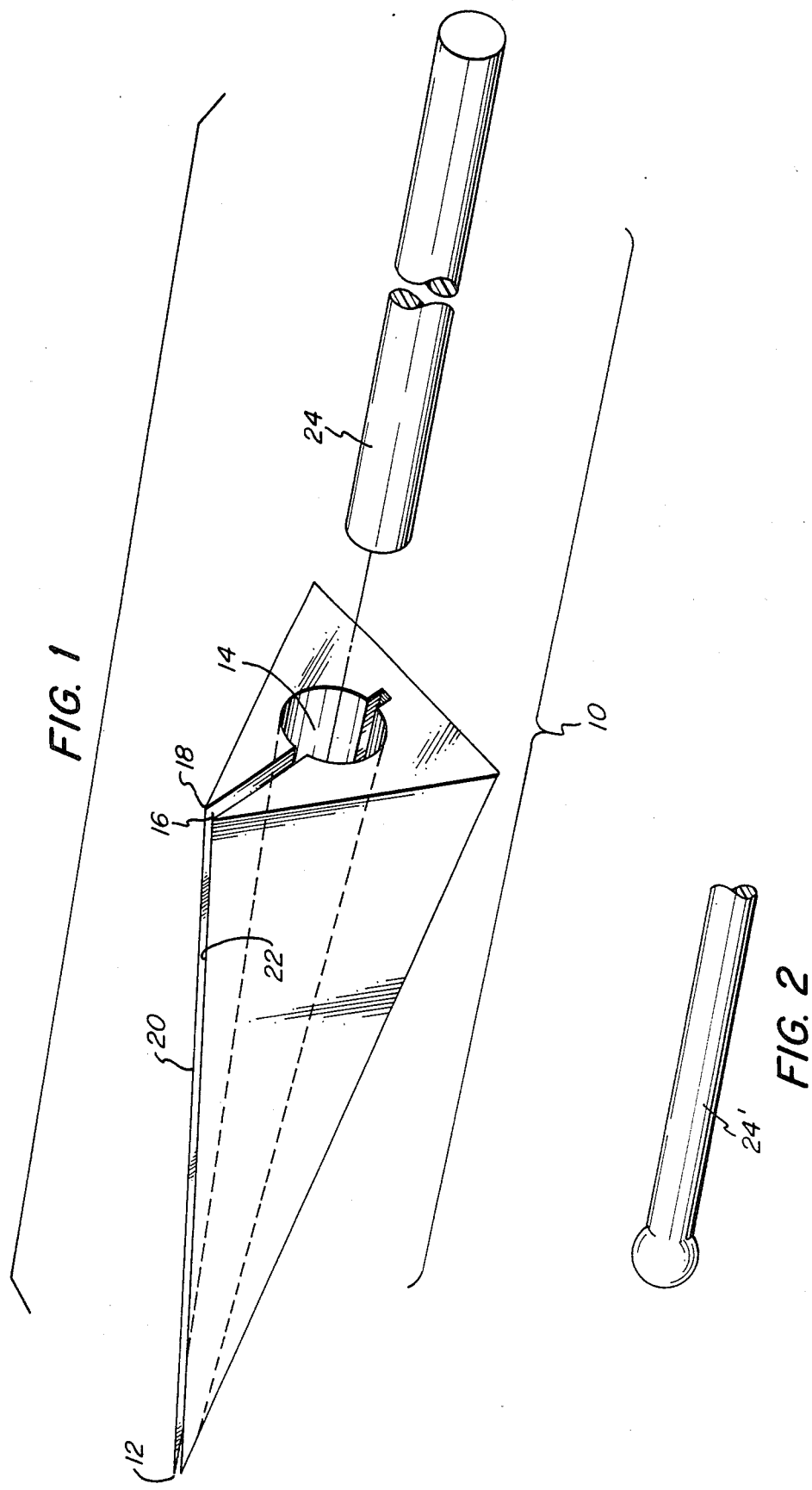

ADJUSTABLE DENTAL WEDGING SYSTEM

TECHNICAL FIELD:

This invention relates to the field of dental instruments and more particularly, to dental wedges which are adjustable.

BACKGROUND OF THE INVENTION:

Dental wedges are well known in the art and have been used extensively for over a century. As is well known, each tooth ideally contacts the next only at the top surfaces thereof. When repairs are needed on a tooth, the tooth is separated from adjoining teeth by a dental wedge. A dental matrix, typically a metal band, is then inserted around the tooth to hold filler material.

Most wedges are of a basic trihedron shape and taper to a point. In use, the wedge is inserted in the gap between adjacent teeth to further separate them so that repairs can be performed. The amount of separation between teeth depends on the size of the wedge which is used.

Since the dental wedge is limited in length, a plurality of wedges must be available to accommodate all the different sizes needed for the different intertooth gaps and the amount of separation which may be needed. Examples of such wedges include the dental separating wedge disclosed in U.S. Pat. No. 3,000,079 and U.S. Pat. No. 3,636,631.

Other types of dental wedges include the trihedron dental wedge of U.S. Pat. No. 3,890,714, which is characterized by a plurality of serrated openings.

U.S. Pat. No. 4,259,070 teaches a variation on the trihedron wedge wherein a pair of disposed interfitting circular-bodied wedges are interposed between teeth. U.S. Pat. No. 2,867,905 also discloses a trihedron type dental wedge having a sheath. U.S. Pat. No. 1,806,718 discloses a dental wedge comprised of a plurality of tapered sections used in a fashion similar to those described hereinabove.

Other dental wedge embodiments include the tapered C-shaped dental wedge disclosed in U.S. Pat. No. 4,578,035; the dental matrix of U.S. Pat. No. 532,722; and the tooth-spreader wedge of U.S. Pat. No. 819,136.

Dental wedges disclosed in the prior art are incapable of varying the tooth separation once the wedge is put in place between adjacent teeth. This has not been a problem with conventional amalgam fillers, as such fillers are somewhat viscous and can be packed against the matrix, slightly expanding the matrix toward the adjoining teeth. When the matrix and wedges are removed, the adjoining teeth will return and again contact the adjoining teeth at the top surface.

However, with newer composite type fillers there is insufficient viscosity to allow for packing. Consequently, when a conventional dental matrix and wedges are removed, a gap will remain between teeth at their top surfaces. It would therefore be advantageous to have an improved dental wedge for use with the newer composite materials. The present invention provides such a wedge which is adjustable to vary the separation between adjacent teeth.

SUMMARY OF THE INVENTION

The present invention provides a dental wedging system that can be adjusted to provide adequate intertooth separation.

According to the present invention, an adjustable dental wedge of resilient material has a central bore positioned along a longitudinal axis. The wedge is characterized by a plurality of opposed leaves formed along the longitudinal axis. The leaves separate along an apex of the wedge.

According to another aspect of the present invention, an adjustable dental wedging system includes a resilient dental wedge having a central bore positioned parallel to a longitudinal axis thereof. The wedge further includes a plurality of opposed leaves formed along a longitudinal axis which separate along an apex of the wedge. Also included is a piston having an end for cooperating with the wedge bore so that the leaves separate from the apex in response to the piston moving along the longitudinal axis.

BRIEF DESCRIPTION OF THE DRAWINGS

FIG. 1 is an expanded perspective illustration of an adjustable dental wedging system provided according to the present invention; and FIG. 2 is a perspective view of an alternate embodiment of a plunger that can be used in conjunction with the wedge portion of FIG. 1.

DETAILED DESCRIPTION OF THE INVENTION

Referring now to FIG. 1, there is illustrated in perspective an adjustable dental wedging system 10 provided according to the present invention. In a preferred embodiment, the adjustable wedge has an overall trihedron shape tapering to a tip 12 at one end, although those skilled in the art will note that other wedge shapes can be substituted. Typically, the wedge is disposable, comprised of polyvinyl plastic or equivalent resilient material.

Within the dental wedge is an axial, tapered bore 14 extending down the length of the wedge toward the tapered tip. The wedge is further characterized by a slit 16 which extends from corner 18 of the trihedron wedge toward the tapered tip such that the wedge can be approximately subdivided into two leaves 20 and 22.

In use, the dental wedge is first placed between adjacent teeth, tapered end in first, and positioned to provide an initial separation. As is well known, the separation between the teeth is necessary to compensate for the thickness of a metallic band which is a portion of a conventional dental matrix (not shown) used in dental reconstruction, such as to fill cavities in the teeth. Proper tooth reconstruction requires that the teeth come in contact at a region near the top surface of the tooth. If the teeth were not separated during reconstruction of the tooth, there would be an undesirable gap between the filled tooth and the adjacent tooth at the top surface.

Dental wedges of the prior art have been successfully used where the filling material comprises a conventional silver alloy compound (amalgam) or equivalent. The silver compound itself is characterized by a high viscosity that allows for packing. The packed compound has sufficient consistency to extend the matrix slightly against the adjacent teeth and maintain its shape. Therefore, only a partial separation of the teeth is required of a wedge.

Improvements in technology have resulted in filling compounds which are of a composite design possessing a very low viscosity initially. The new compounds cannot expand the matrix. Consequently, when dental wedges of the prior art have been used, a small undesirable gap remains after the matrix is removed. However, with an adjustable dental wedging system provided according to the present invention, once a composite filling compound has been first positioned in the matrix, a piston 24 can be inserted in the bore 14 of the wedge, forcing the two leaves 20, 22 further apart. Typically, the dentist will first insert the wedging system of the present invention between the tooth under reconstruction and adjacent tooth. After a conventional dental matrix has been positioned around the damaged tooth, the composite material is put into the matrix. Since the amalgam is of a low viscosity, it cannot be packed and consequently the matrix remains unextended. Piston 24 is now inserted into bore 14, forcing the leaves 20, 22 apart to provide additional working space between the teeth for completion of the filling. The teeth which contact the leaves are forced further apart. A piston is held in place for the short time needed to allow the composite material to harden.

In a preferred embodiment, the piston 24 is a cylinder having a diameter whose magnitude is selected to engage and begin to move apart the leaves approximately one-half way down the length of the wedge. Although a cylindrical piston is shown in FIG. 1, those skilled in the art will note that other piston designs, such as one with an approximately spherical head for engaging the bore as shown in FIG. 2, may be substituted. The piston may be made from the same material as the wedge itself. Typically, the wedge and piston are made from the same material in the same mold such that a single wedge and piston remain connected by a plastic tether. As a unit, the wedge and piston may be conveniently taken and inserted into the mouth so the piston can be easily located and pushed into the bore when necessary.

Similarly, although the invention has been described with respect to a preferred embodiment thereof, those skilled in the art will note that additions, deletions or substitutions thereto can be made therein consistent with the spirit and scope of the invention.

I claim:

1. An adjustable dental wedge, comprising:
    a wedge of resilient material having a central bore positioned parallel to an axis, said wedge being essentially a trihedron, said wedge further having two opposed leaves formed along said axis separating from said bore to one apex of said wedge.

2. The adjustable dental wedge of claim 1 wherein the resilient material comprises polyvinyl plastic.

3. An adjustable dental wedging system, comprising:
    a wedge of resilient material having a tapered, central bore positioned parallel to an axis, said wedge being essentially a trihedron, said wedge further having two opposed leaves formed along said axis, separating from said bore to one apex of said wedge; and
    a piston having an end for cooperating with said tapered, wedge bore so that said leaves separate from said apex in response to said piston moving along said axis.

4. The adjustable dental wedging system of claim 3 wherein said piston is comprised of resilient material.

5. The adjustable dental wedging system of claim 4 wherein said resilient material comprises polyvinyl plastic.

6. The adjustable dental wedging system of claim 4 further comprising tethering means for affixing said piston to said trihedron, enabling said adjustable dental wedging system to be located between adjacent teeth as a unit.

7. The adjustable dental wedging system of claim 4 wherein said piston end is approximately spherical.

* * * * *